United States Patent [19]

Heil, Jr. et al.

[11] Patent Number: 5,397,342

[45] Date of Patent: Mar. 14, 1995

[54] RESILIENT STRUCTURALLY COUPLED AND ELECTRICALLY INDEPENDENT ELECTRODES

[75] Inventors: Ronald W. Heil, Jr., Roseville; Bruce H. Kenknight, Robbinsdale; Robert W. Wickham, Jr., deceased, late of Harris; by Duane R. Quiggle, legal administrator, Forest Lake, all of Minn.

[73] Assignee: Cardiac Pacemakers, Inc., St. Paul, Minn.

[21] Appl. No.: 71,859

[22] Filed: Jun. 7, 1993

[51] Int. Cl.[6] ............................................. A61N 1/05
[52] U.S. Cl. .................................. 607/129; 128/642; 607/5
[58] Field of Search ........ 607/119, 122, 123, 125–132, 607/5; 128/642

[56] References Cited

U.S. PATENT DOCUMENTS

| | | |
|---|---|---|
| 3,333,045 | 7/1967 | Fisher et al. . |
| 3,472,234 | 8/1967 | Tachick ................. 607/131 |
| 4,270,549 | 7/1981 | Heilman . |
| 4,567,900 | 2/1986 | Moore . |
| 4,662,377 | 5/1987 | Heilman et al. . |
| 4,699,147 | 10/1987 | Chilson et al. ................. 128/642 |
| 4,865,037 | 9/1989 | Chin et al. . |
| 4,938,231 | 7/1990 | Milijasevic et al. . |
| 4,971,070 | 11/1990 | Holleman et al. . |
| 4,998,975 | 3/1991 | Cohen et al. . |
| 5,010,894 | 4/1991 | Edhag ................. 607/128 |
| 5,033,477 | 7/1991 | Chin et al. . |
| 5,042,463 | 8/1991 | Lekholm . |
| 5,044,375 | 9/1991 | Bach, Jr. et al. . |
| 5,052,407 | 10/1991 | Hauser et al. . |
| 5,107,834 | 4/1992 | Ideker et al. . |

FOREIGN PATENT DOCUMENTS

| | | |
|---|---|---|
| 0009732 | 4/1980 | European Pat. Off. ............ 607/123 |
| 0211166 | 2/1987 | European Pat. Off. . |
| 0417031 | 3/1991 | European Pat. Off. . |
| 0479435 | 4/1992 | European Pat. Off. . |

OTHER PUBLICATIONS

Berens et al., "New Stable . . . Pacing Loop", American Journal of Cardiology, vol. 34, Sep. 1974, pp. 325–332.

*Primary Examiner*—Lee S. Cohen
*Assistant Examiner*—Jeffrey R. Jastrzab
*Attorney, Agent, or Firm*—Haugen and Nikolai

[57] ABSTRACT

A cardioversion/defibrillation device includes a lead catheter housing, two electrically independent conductors, and a pair of resilient helically coiled electrodes, one electrode coupled to each of the conductors. The distal ends of the electrodes are contained within an insulative, resilient coupling sleeve, such that the electrodes and sleeve form a loop when in the relaxed state, with the electrodes electrically isolated from one another. To facilitate body insertion and delivery to the electrode placement site, the electrodes and coupling sleeve are loaded into a delivery cannula, which elastically deforms the electrodes and sleeve into an elongate, narrow delivery configuration. Upon release from the delivery device, these components resiliently return to the loop configuration. If desired, an inextensible filament secured to the coupling sleeve is pulled proximally after deployment to selectively reconfigure the electrodes into two loops. Another modification involves several linear electrode branch segments, coupled to each electrode and projected inwardly of the loop or loops formed by the electrodes.

20 Claims, 6 Drawing Sheets

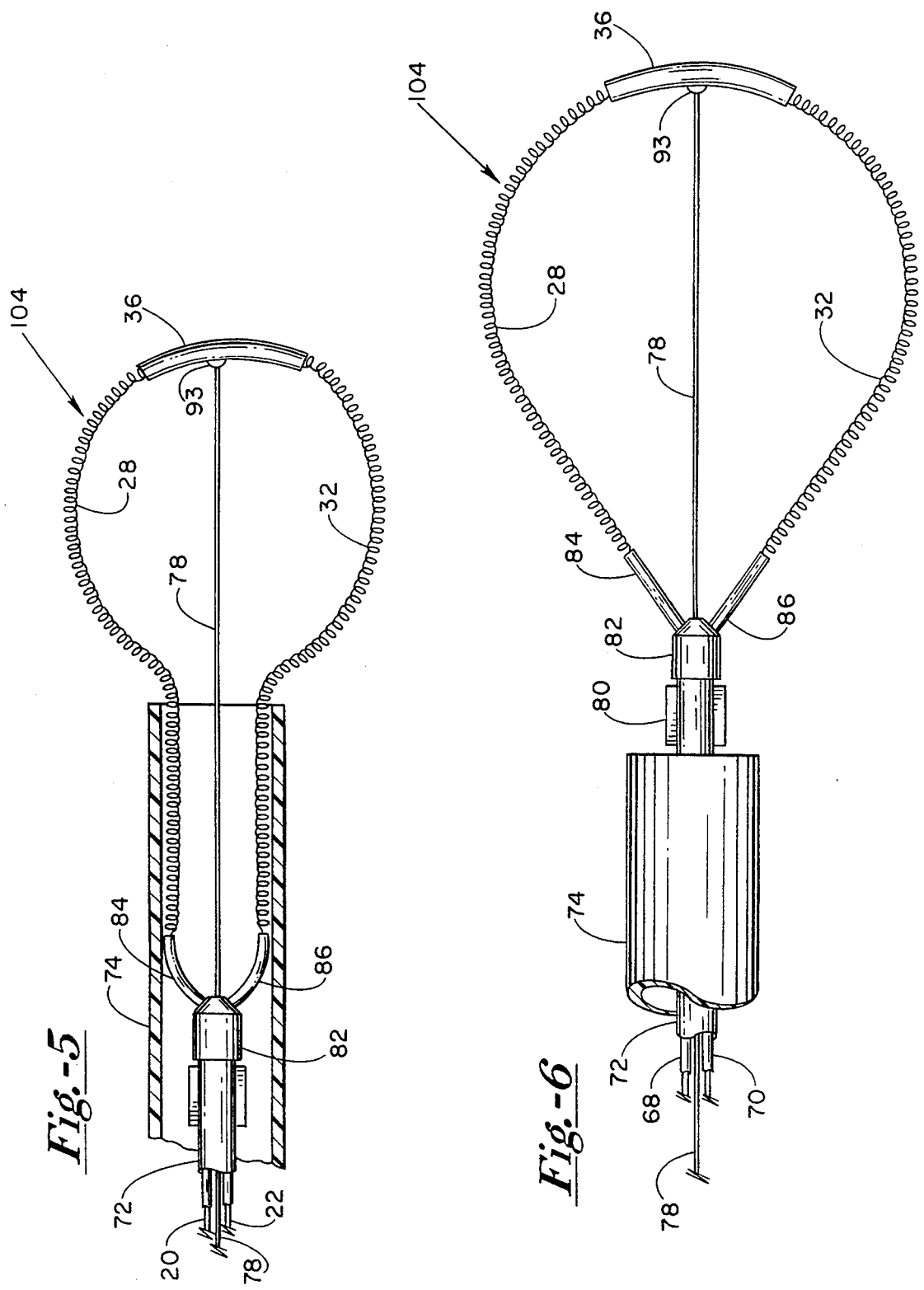

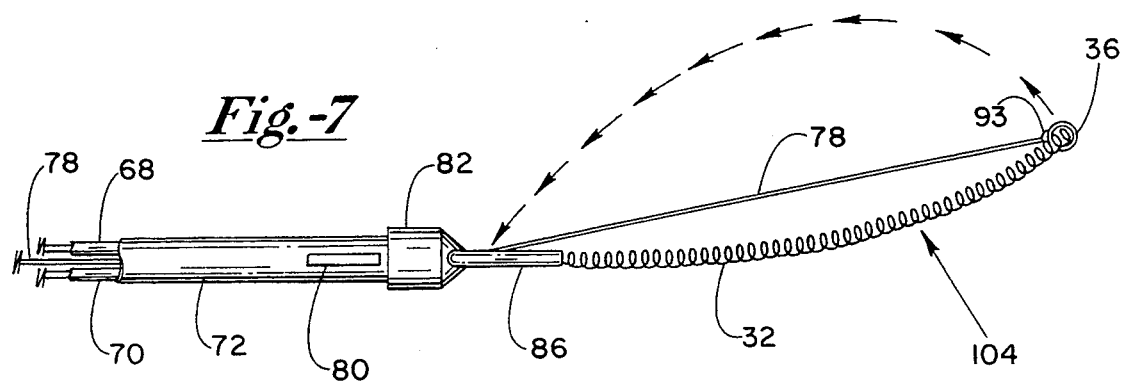
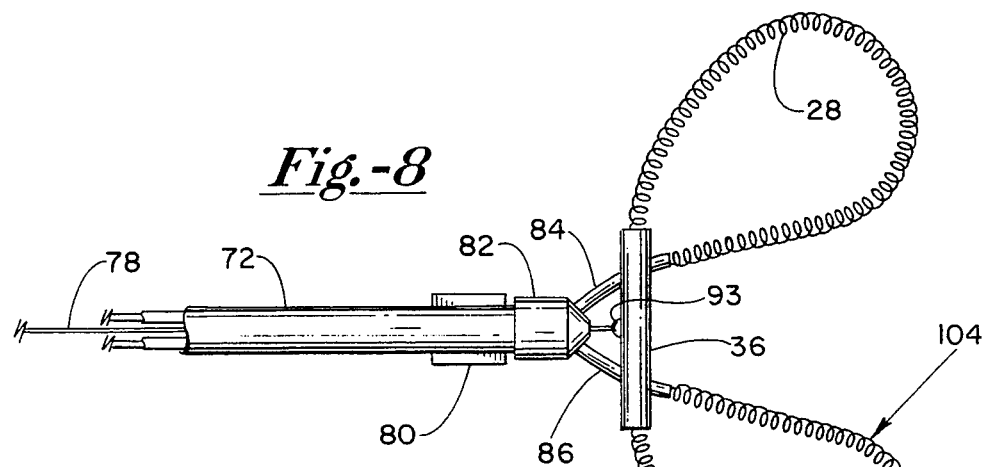
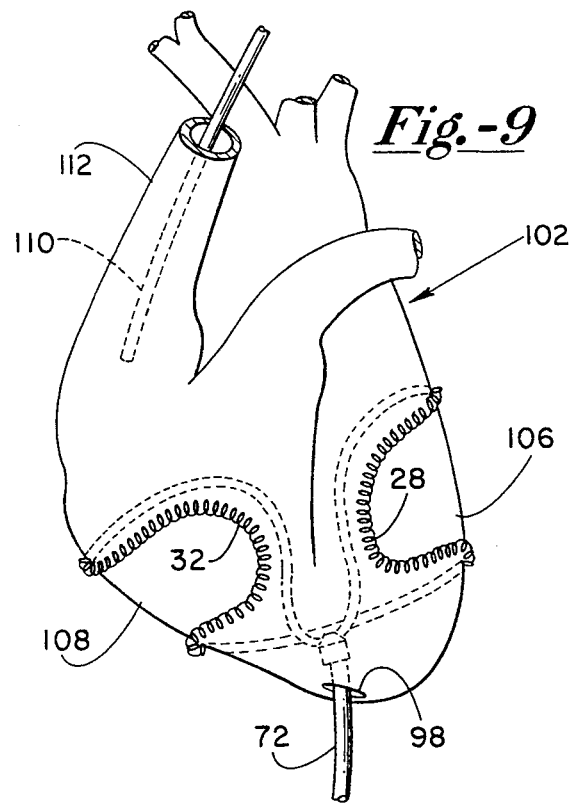

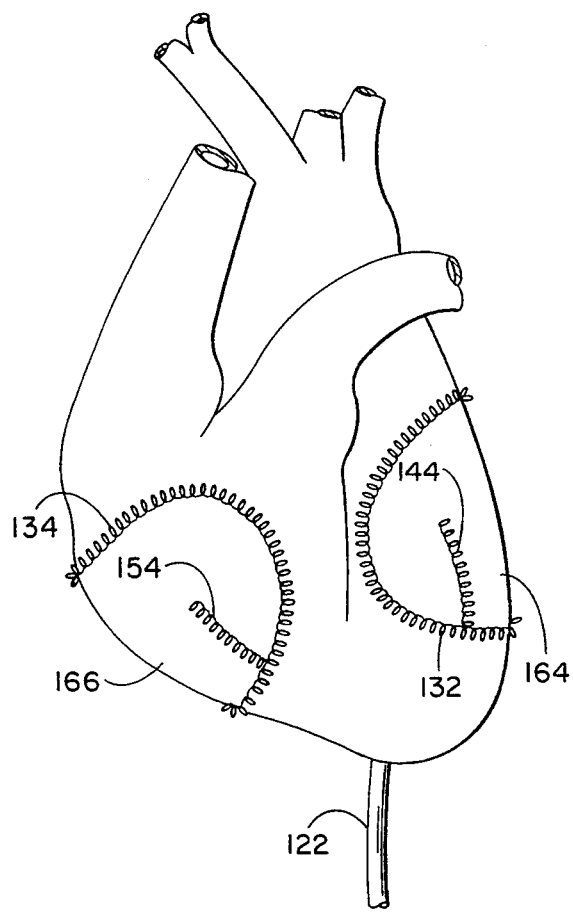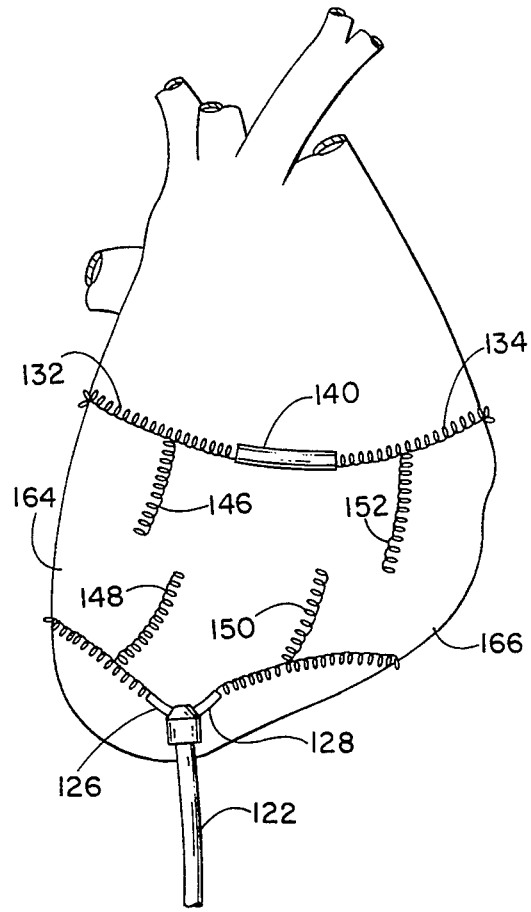

RESILIENT STRUCTURALLY COUPLED AND ELECTRICALLY INDEPENDENT ELECTRODES

BACKGROUND OF THE INVENTION

The present invention relates to body implantable tissue stimulation electrodes, e.g. for cardiac pacing or cardioversion/defibrillation, and more particularly to the deployment and implantation of such electrodes.

Heart disease is a major cause of deaths in the United States and in other industrialized nations. One well known treatment approach utilizes an implantable cardiac pacing device, through which relatively mild periodic electrical impulses are applied to epicardial or endocardial tissue as necessary to maintain normal sinus rhythm. More recently, cardioversion/defibrillation devices have been developed to counteract tachyarrhythmias (rapid disturbances in cardiac electrical activity). In particular, the conditions of ventricular tachycardia, ventricular flutter and ventricular fibrillation are widely believed to be the primary cause of sudden deaths associated with heart disease. Defibrillation devices also are utilized to counteract atrial tachyarrhythmic conditions, although such conditions are not considered life threatening unless they lead to a rapid ventricular disturbance.

Tachyarrhythmic conditions frequently can be corrected by applying relatively high energy electrical shocks to the heart, a technique often referred to as cardioversion. Cardioversion devices include implantable electronic standby defibrillators which, in response to the detection of an abnormally rapid cardiac rhythm, discharge sufficient energy through electrodes connected to the heart to depolarize and restore the heart to normal cardiac rhythm.

Cardioversion/defibrillation devices frequently include epicardially implanted electrodes. The surgical procedure required for implantation, i.e. thoracic surgery such as a median sternotomy or thoracotomy, is highly invasive and presents significant risks to the patient. Examples of epicardial defibrillation electrodes are found in U.S. Pat. No. 4,567,900 (Moore), U.S. Pat. No. 4,291,707 (Heilman et al), and U.S. Pat. No. 4,860,769 (Fogarty et al). A pair of differently biased (e.g. oppositely polarized) epicardial electrodes can be employed, as shown in Moore. Alternatively, the Heilman patent discloses an intravenously inserted endocardial electrode arrangement in combination with a patch electrode positioned near the left ventricular apex.

U.S. Pat. No. 4,270,549 (Heilman) describes a technique for inserting and placing defibrillation electrodes, involving intravenous insertion of an endocardial electrode in combination with a patch electrode inserted through a skin incision and through a tunnel created inside the thorax and outside the pleural cavity. Alternatively, U.S. Pat. No. 4,865,037 (Chin et al) discloses a technique for inserting separate electrodes into the intrapericardial space through catheters. An incision is formed in the upper abdominal wall. Then, tissues between the incision and the pericardium are separated, and an incision is then made in the pericardium. A cannula containing a defibrillation electrode is inserted through these incisions, to enable positioning of the electrode in the pericardium. A second cannula containing a second electrode is inserted on the opposite side of the heart, in the same manner.

The above described approaches have enjoyed limited success, yet present risks to patients due to the time and complexity involved. The intravascular approach gives rise to a risk of superior vena cava syndrome, pulmonary embolism, endocardial shock-induced tissue damage, and endocarditis. Left thoracic subcutaneous patches involve discomfort to the patient, and the risk of transcutaneous erosion, subcutaneous infection and fatigue fracture.

Fixation of epicardial electrodes gives rise to difficulties. Active fixation of electrodes, particularly near their free ends, is required to prevent post implantation migration, yet such fixation creates the risk of epicardial lacerations, abrasions and other trauma. Another problem, particularly with patch electrodes, is the current density gradient, i.e. maximum current density regions at the patch periphery. Current density gradients reduce the efficacy of the electrode, in terms of the ratio of useful cardioversion/defibrillation energy as compared to required pulse generator output energy.

Therefore, it is an object of the present invention to provide a tissue stimulation device including two or more differently polarized electrodes, deployable simultaneously using minimally invasive techniques.

Another object is to provide a device for simultaneously deploying multiple, differently biased electrodes within the pericardium.

A further object is to provide a means for deploying an array of resilient electrodes, and for selectively altering the shape of the array following deployment.

Yet another object is to provide an electrode array having a loop configuration and means associated with the loops for reducing current density gradients.

SUMMARY OF THE INVENTION

To achieve these and other objects, there is provided a body implantable tissue stimulation device. The device has an electrode array comprising a resilient, elongate and electrically conductive first electrode, an elongate, resilient and electrically conductive second electrode, and an electrically insulative connecting means for securing the first and second electrodes relative to one another. The electrode array tends to assume a loop configuration when in a relaxed state. Each of the electrodes has an exposed exterior surface over a majority of the electrode length. Each electrode further is electrically isolated from the other electrode when the electrode array is in the loop configuration. The stimulation device further includes an elongate and flexible first conductor having a distal end portion electrically coupled to the first electrode. A proximal end of the first conductor is adapted for coupling to an electrical pulse generator, for conducting electrical pulses between the pulse generator and the first electrode. Likewise an elongate and flexible second conductor has a distal end region electrically coupled to the second electrode. A proximal end of the second conductor is adapted for coupling to the pulse generator, for conducting electrical pulses between the pulse generator and the second electrode. The first and second conductors are electrically isolated from one another. An electrode deployment means is operatively associated with the electrode array, for confining the electrode array elastically compressed against a restoring force, i.e. in a delivery configuration. This facilitates a body insertion and delivery of the electrode array to a predetermined stimulation site within the body. The deployment means is controllable from a proximal region of the first and second conductors to effect a release of the electrode array at the stimulation site. Upon release, the electrode array returns to the loop configuration under the restoring force.

Preferably the device further includes a control means coupled to the electrode array for selectively elastically deforming the electrode array, after its release, into a deployment configuration in which a first and second electrodes remain electrically isolated from each other. One advantageous form of control means is a substantially inextensible filament attached at one of its ends to the electrode array and extending proximally along the conductors. When pulled proximally, the filament elastically deforms the electrode array. Then, a latching means secures the filament, to maintain the filament against distal movement responsive to the elastic restoring force in the array.

The device further can include a lead catheter with lumen means for containing the first and second conductors adjacent but electrically isolated from one another. The distal end of the lead catheter is advantageously located at the respective distal end regions of the conductors, to facilitate anchoring of the electrode array with a suture or other securement means at the lead catheter distal end.

The insulative connecting means includes the distal end of the lead catheter. The connecting means further includes an insulative coupler fixed to the respective distal end portions of the first and second electrodes to maintain the distal end portions in spaced apart relation to one another. The inextensible filament preferably is attached to the insulative coupler.

In one advantageous arrangement, the electrodes form a single closed loop when in the loop configuration, and two side by side loops when in the deployment configuration. If desired, one of the loops can be somewhat larger than the other, to facilitate positioning the loops over the apecies of the left and right ventricles.

Another aspect of the present invention is a body implantable tissue stimulation device, including a resilient tissue stimulating electrode means with at least one elongate resilient curvelinear electrode. The electrode has an exposed exterior surface over the majority of its length and is curvelinear when in a relaxed state to define a periphery of a loop. The electrode means further includes a plurality of substantially linear electrode branch segments. Each branch segment is electrically coupled at one end to the curvelinear electrode and directed inwardly of the loop. An elongate and flexible conductor means has a distal end region electrically coupled to the curvelinear electrode. A proximal end of the conductor means is adapted for coupling to an electrical pulse generator for transmitting electrical pulses between the pulse generator and the electrode means. An electrode deployment means is adapted for releasably confining the electrode means in a compressed delivery configuration against an elastic restoring force, thus to facilitate a body insertion and delivery of the electrode means to a predetermined stimulation site within the body. The electrode deployment means is controllable to release the electrode means. Upon release, the electrode means returns to the loop configuration under the restoring force.

The stimulation device is advantageously configured to incorporate several curvelinear electrodes, each with its own set of branch segments. Each of the several electrodes can be electrically isolated from every other electrode, at least when the electrode means is in the relaxed state.

The provision of at least two electrodes, electrically isolated from one another, facilitates the simultaneous deployment of all electrodes necessary for a complete tissue stimulation system for cardioversion/defibrillation. A complete system including pulse generator, differently biased electrodes, and independent leads for conducting pulses between the pulse generator and the respective electrodes, can be implanted in a single surgical procedure, and with a minimally invasive approach utilizing an incision in the subcostal or subxiphoid region. The loop configuration of the electrodes is particularly well suited for electrode positioning within the pericardium. More particularly, the pericardial sack tends to form the electrode loop (or loops) in a flat, wrapping configuration about the heart. The inwardly extending branch segments tend to reduce current density gradients, which improves tissue stimulation shock efficacy for a given pulse generator power level. Finally, the inextensible filament or other tether enables a selective reshaping of the electrodes, following their release, into a configuration suitable for implantation.

IN THE DRAWINGS

For a further understanding of the above and other features and advantages, reference is made to the following detailed description and to the drawings, in which:

FIGS. 4–8 are diagrammatic views illustrating positioning, release and reconfiguration of a pair of system electrodes;

FIG. 9 illustrates an exemplary deployment of the electrodes;

FIGS. 12 and 13 are diagrammatic views illustrating an exemplary endocardial deployment of the electrodes.

DETAILED DESCRIPTION OF THE PREFERRED EMBODIMENTS

Figure 1:
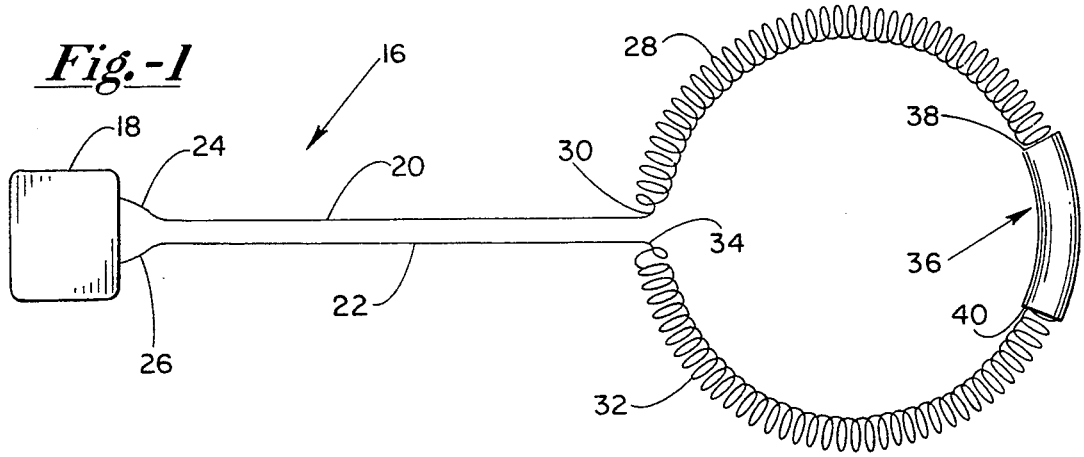
FIG. 1 is a schematic view of a cardioversion/defibrillation system constructed according to the present invention.

Turning now to the drawings, there is shown in FIG. 1 a cardioversion/defibrillation system 16 for selectively applying relatively high energy electrical shocks to the heart, a technique frequently referred to as cardioversion. Typically a cardiac sensing system (not illustrated) is employed with system 16, for detecting an abnormally rapid cardiac rhythm. In response to such detection, a high energy shock is discharged through electrodes contiguous with cardiac tissue to depolarize and restore the heart to normal cardiac rhythm.

System 16 includes a cardioversion pulse generator and control unit 18, and two elongate electrical conductors 20 and 22 coupled to the cardioversion control unit at their respective proximal ends 24 and 26. An electrode 28 is connected to a distal end 30 of a conductor 20. Likewise, an electrode 32 is coupled to the distal end 34 of conductor 22. Electrodes 28 and 32 combine to provide an electrode array.

An electrically insulative coupling sleeve 36, secured to respective distal ends 38 and 40 of electrodes 28 and 32, maintains these distal ends proximate to but electrically isolated from one another. Conductors 20 and 22 are electrically isolated from one another, typically by being encased individually within dielectric tubing, or contained within separate lumens of an insulative catheter. By contrast, each of electrodes 28 and 32 is exposed over nearly all of its length, for maximum surface contact with body tissue when the electrodes are implanted. However, insulative sleeves surround the electrodes at their proximal ends, to ensure that when the electrodes assume a loop configuration as illustrated in FIGS. 1 and 9, they are electrically independent of one another. The electrodes and dielectric sleeves are constructed of resilient, elastically deformable materials. When in a relaxed state, i.e. when subject to no external stress, these components in cooperation tend to assume a loop configuration, i.e. the single, somewhat circular loop illustrated in FIG. 1. So long as the electrodes remain in the loop configuration, they are physically separated and thus electrically independent from one another. Thus electrodes 28 and 32 can be employed as a cardioversion/defibrillation pair, with tissue stimulation pulses generated at cardioversion control unit 18 being transmitted from one electrode to the other via body tissue.

Figure 2:
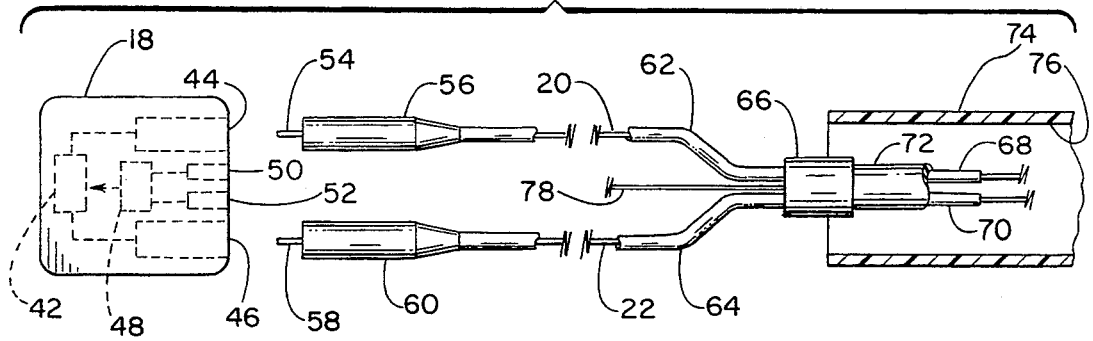
FIG. 2 is an enlarged view of a proximal end region of the system, along with the proximal end of a device used to deploy the system electrodes.
Figure 3:
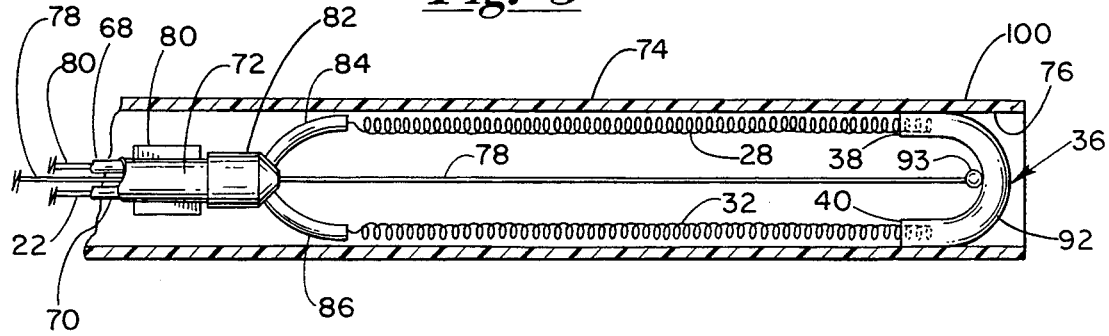
FIG. 3 is an enlarged view of a distal end region of the system and the deployment device.

FIGS. 2 and 3 illustrate system 16 in greater detail, and show a delivery cannula 74 employed to facilitate body insertion and positioning of electrodes 28 and 32. Cardioversion control unit 18 includes a cardioversion pulse generating circuit, represented schematically in FIG. 2 at 42. Two receptacles 44 and 46 are electrically coupled to the pulse generating circuit. The control unit further includes pulse or heart rate sensing circuit represented schematically at 48. A pair of receptacles 50 and 52 receive a plug, boots or other appropriate coupling devices to electrically couple a pair of sensing electrodes (not shown) to the control unit. Sensing circuit 48 and cardioversion circuit 42 are operatively coupled to one another, in that when an abnormal rhythm or pulse rate is sensed in sensing circuit 48, cardioversion circuit 42 is triggered to deliver a cardioversion pulse.

At the proximal end of conductor 20 is a pin 54, surrounded by insulative boot 56. Conductor 22 similarly includes a pin 58 surrounded by a boot 60. Receptacles 44 and 46 in cardioversion control unit 18 receive pin 54 and boot 56, and pin 58 and boot 60, respectively, to electrically couple conductors 20 and 22 with the cardioversion pulse generating circuit. Each boot includes ribs or grooves, and is maintained in its associated receptacle in a fluid tight friction fit, to isolate its associated conductor from body fluids.

Distally of the boots, conductor 20 is surrounded by an electrically insulative and fluid tight sheath 62, and conductor 22 is surrounded by a similar sheath 64. Conductors 20 and 22 preferably are highly compliant and resistant to fatigue. The conductors can be formed of low resistance composite materials such as drawn braised stranded (DBS) or drawn filled tubes (DFT), coated with platinum or another metal from the platinum group, e.g. iridium, ruthenium or palladium. The strands can be formed of titanium or platinum. A suitable DFT conductor is composed of a silver core within a stainless steel tube. The conductors can be single cables or strands as shown, or multiple wires in a twisted or braided arrangement. In any event, the conductors and sheaths are preferably highly compliant and pliable.

Distally of a reinforcing and strain relief member 66, conductors 20 and 22 are surrounded by sheaths 68 and 70, which in turn are contained within the lumen of an elongate lead catheter 72. Catheter 72 is dielectric and highly compliant, and maintains the conductors and sheaths adjacent one another over the length of the catheter. The sheaths electrically isolate the conductors from one another, despite their proximity. Catheter 72 and all sheaths can be constructed of a suitable body compatible polymer, e.g. a medical grade silicone rubber or polyurethane.

FIG. 2 illustrates the proximal end of a delivery cannula 74 having a lumen 76 containing the conductors, sheaths and catheter. Also contained within lumen 76 is an inextensible filament 78, preferably constructed of a high tensile strength, body compatible material such as Kevlar (brand) polymer or other synthetic material. The delivery cannula surrounds catheter 72 substantially over the entire catheter length, and extends distally beyond catheter 72 to contain electrodes 28 and 32 as well. As seen in FIG. 3, an anchoring element 80 is mounted to the distal end of lead catheter 72, to facilitate securing the lead distal end to body tissue. Anchoring element 80 can be a conventional polymeric suture sleeve designed to secure the lead distal end to adjacent body tissue using a suture. Or, as shown, anchoring element 80 can be a sleeve provided with one or more tabs for securing the lead end to adjacent tissue using a surgical staple. Beyond catheter 72, conductors 20 and 22 are contained in a reinforcing and strain relief member 82. Dielectric sleeves 84 and 86 extend distally of the strain relief member, and surround electrodes 28 and 32, respectively, distally of the strain relief member. Each electrode is mechanically and electrically coupled to its associated conductor, either within the strain relief member or within its associated sleeve.

Electrodes 28 and 32 preferably are formed from either single or multi-filar helical coils of titanium wire coated with platinum. Typically, the electrode wires have diameters in the range of 0.005–0.010 inches. The distal end of each electrode is contained within insulative coupling sleeve 36 as indicated in broken lines at 38 and 40, respectively.

Coupling sleeve 36 is a resilient tube, and when in the relaxed state is substantially linear. When not subject to external stresses, coupler sleeve 36 tends to assume its linear configuration. Thus, due to their resilience and their interconnection, electrodes 28 and 32, and sleeves 36, 84 and 86, all cooperate to provide an electrode array that tends to assume the loop configuration illustrated in FIG. 1. When contained in lumen 76, however, sleeves 84 and 86 are biased towards one another, a bend is formed along the medial region 92 of sleeve 36, and electrodes 28 and 32 are brought into close proximity and can contact one another, although shown as spaced apart from one another in FIG. 3.

Filament 78 is secured to medial region 92 of sleeve 36, and extends in the proximal direction through catheter 72 until it emerges from the proximal end of the catheter as shown in FIG. 2. The preferred element for securing the filament is a spherical bead 93 at the distal end of the filament. Bead 93 preferably is formed of a hard (high durometer) material such as polypropylene, polysulfone, Teflon or glass. A receptacle (not shown) in strain relief member 82 is open in the direction toward bead 93, and is selectively sized to capture and retain the bead due to friction and an elastic retaining force of the strain relief member.

One of the salient features of the present invention is that it enables the simultaneous delivery and deployment of two or more electrically independent biased electrodes employing a minimally invasive subxiphoid or subcostal surgical approach to the pericardial space.

Figure 4:
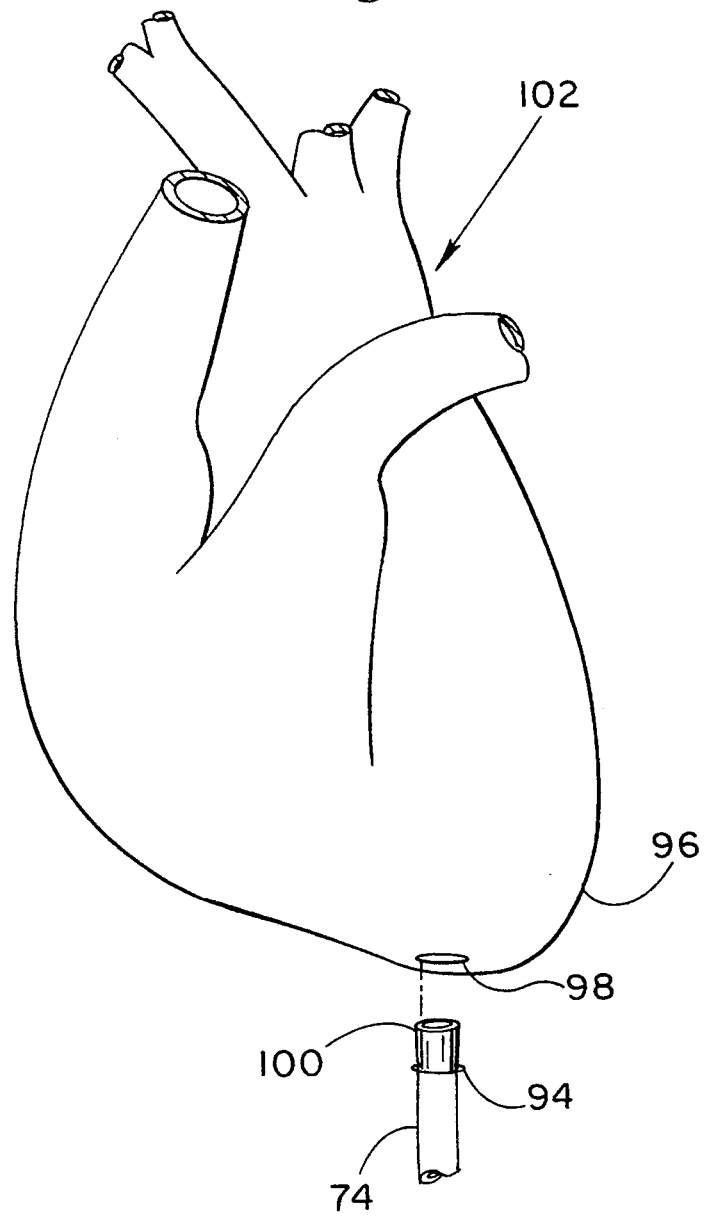

As seen in FIG. 4, the procedure begins with an incision 94 into the body, e.g. a subxiphoid, subcostal or intercostal incision. Tissues between the incision and the pericardium 96 are separated digitally by the surgeon, and a further incision 98 is made in the pericardium. Cannula 74, containing catheter 72 and the electrodes as illustrated in FIG. 3, is inserted into the pericardium via the incisions. Delivery cannula 74 is then selectively maneuvered, to position distal end 100 of the cannula at a selected location between the heart surface 102 and pericardium 96, for release of the electrodes.

The electrode release and deployment sequence is illustrated in FIGS. 5–8. While these figures illustrate only the lead and electrodes (without the heart and pericardium) as a matter of convenience, it is to be understood that the sequence occurs with the electrodes positioned at the selected release location near the heart.

The electrodes are released by moving delivery cannula proximally, while maintaining the position of lead catheter 72, by hand manipulation of the catheter and cannula at their proximal ends. Thus, lead catheter 72 has sufficient axial stiffness to resist axial buckling or compression during proximal movement of cannula 74. The cannula also has the requisite axial stiffness, and further is provided with a longitudinal or axial slit running distally from its proximal end, to facilitate separation (lateral removal) of the delivery cannula from the lead catheter as the cannula is withdrawn. Once free of the catheter, coupling sleeve 36 tends to return to a linear shape under its elastic restoring force, spreading the distal regions of electrodes 28 and 32 apart from one another as seen in FIG. 5. The electrodes and sleeves, once free of delivery cannula 74, assume the loop configuration shown in FIG. 6. The loop configuration consists of a single loop electrode array 104. During release, the pericardium bears against the electrodes, tending to maintain the electrodes against the epicardial surface, and tending to maintain a relatively flat loop array 104. At this point, delivery cannula 74 can be proximally withdrawn.

A final electrode implant shape is achieved by proximally moving filament 78, to draw sleeve 36 proximally against the elastic restoring force of the electrode array. This elastically deforms the electrodes and bends loop 104 as shown in FIG. 7. Continued movement of the filament folds loop 104 over upon itself, with sleeve 36 proximate strain relief member 82 and contacting sleeves 84 and 86, as illustrated in FIG. 8. The electrode array thus is formed into two loops or loop segments, one formed by electrode 28 and the other, by electrode 32. The sleeves are of sufficient length to ensure that the electrodes, when in the implant configuration shown in FIG. 8, remain electrically independent of each other. When the filament has been withdrawn sufficiently to form the electrode array into the implant configuration, it also has moved sufficiently to position spherical bead 93 within the receptacle of strain relief member 82. An elastic restoring force in the strain relief member tends to retain bead 93 within the receptacle. Thus, the implant configuration is maintained, overcoming an elastic restoring force in electrodes 28 and 32 that otherwise tends to move the electrode array toward the loop configuration. The strain relief member and bead thus cooperate to provide a latching means to maintain the implant configuration.

FIG. 9 illustrates one preferred approach to positioning the electrode assembly. Electrode 28 is positioned epicardially on the left ventricle 106, while electrode 32 is positioned on the right ventricle epicardium 108 through a subxiphoid access to the region (pericardial space) between the pericardium 96 and the heart 102. Because the pericardial space is narrow, the pericardium presses against electrodes 28 and 32, to maintain them in close proximity to the epicardium.

While electrodes 28 and 32 as illustrated have substantially the same length, this symmetry is not necessary. In fact, it may be advantages to provide an electrode 28 of greater length than electrode 32, due to the larger mass of the left ventricle as compared to the right ventricle. The placement procedure also can involve further movement of the electrode assembly, to optimize the respective electrode positions to the extent possible. With the electrode assembly positioned as required, the distal end of lead catheter 72 is secured to body tissue, by suturing anchoring element 80, e.g. with a suture or surgical staple. Because of the manner in which electrodes 28 and 32 are maintained between the heart and pericardium, the suturing the lead distal end sufficiently secures the electrodes as well. There is no need to suture the electrodes. There is no need for barbs, hooks or other auxiliary anchoring means along the electrodes. This simplifies implantation and eliminates the potential for injury to tissue as the elecrode assembly is being positioned. Further, the electrodes can be smooth and free of discontinuities, for maximum shock efficiency.

If desired, the complete cardioversion/defibrillation system may employ an intravenously inserted electrode 110 at the superior vena cava 112, with tissue stimulating pulses travelling from either electrode 28 at the left ventricle as an anode, to electrode 32 and electrode 110, both as cathodes. Electrode 110, however, is not essential. Electrodes 28 and 32, because they are electrically isolated from one another, can provide the anode and cathode, respectively for pulses travelling from one ventricle to the other.

Figure 10:
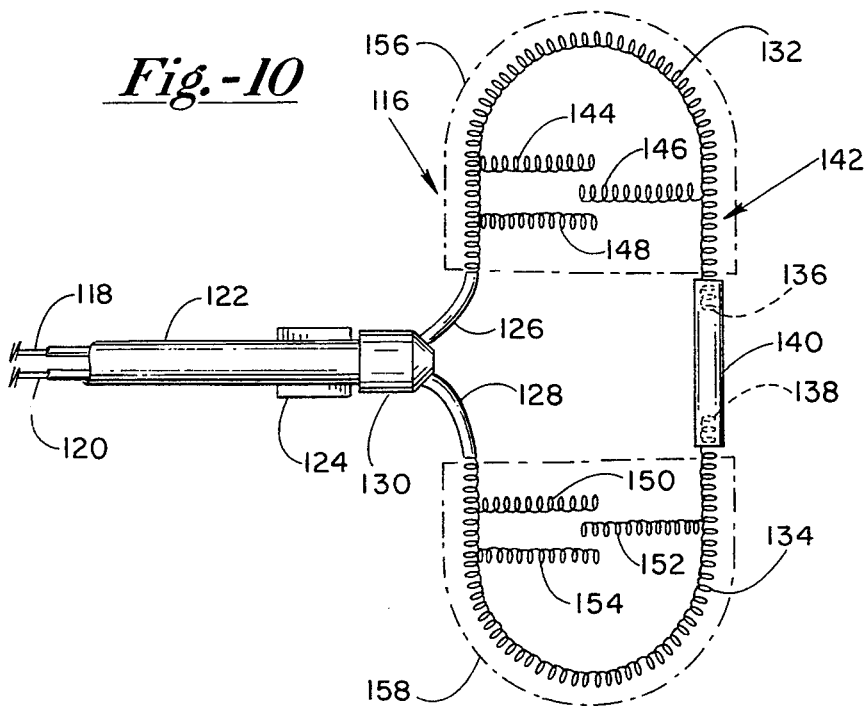
FIG. 10 is a distal end region view of an alternative embodiment electrode array constructed according to the present invention.

FIG. 10 shows the distal region of an alternative cardioversion/defibrillation device 116. The device includes two conductors 118 and 120, contained within separate lumens of an electrically insulative lead catheter 122. An anchoring element 124 is provided near the distal end of the lead catheter. A pair of electrically insulative sleeves 126 and 128 extend from a strain relief member 130 at the lead catheter distal end. An elongate flexible coil electrode 132 includes a proximal region contained within sleeve 126 and coupled to conductor 118. Similarly, an elongate and flexible coil electrode 134 has a proximal portion contained within sleeve 128 and is electrically coupled to conductor 120. Respective distal end portions of the electrodes, indicated at 136 and 138, are contained within an electrically insulative and resilient coupling sleeve 140. In the relaxed state, the electrodes and sleeves tend to assume a loop configuration, i.e. a loop array 142 as shown in FIG. 10.

Several conductive electrode branch segments are provided along each of the electrodes. Branch segments 144, 146 and 148 are electrically coupled to electrode 132 and project inwardly of loop array 142. Similar linear branch segments 150, 152 and 154 are coupled to electrode 134, and likewise project inwardly of the loop. These branch segments, like the electrodes themselves, are formed of resilient, metallic, helically wound multifilament coils. Preferably, the adjacent branch segments of each electrode interdigitate or extend beyond the free ends of one another, as illustrated in FIG. 10. Regardless of whether the branch segments interdigitate, their inward extension counteracts what is commonly known as "edge effect." More particularly, each of coil electrodes 132 and 134 has an effective or "phantom" shocking area. These phantom areas are shown in broken lines at 156 and 158. Without any branch segments, the shocking potential of each coil electrode would be concentrated along the coil itself, i.e. along the periphery of the phantom area. In other words, with respect to each coil electrode, there would be an undesirable potential gradient from the periphery to the center of the phantom area. The branch segments substantially reduce this gradient, for a more consistent potential level over the entire phantom area. The density or distribution of current flow, through tissue from electrode 132 to electrode 134, is more uniform over the electrode phantom areas, as opposed to current densities much greater near the perimeters of these phantom areas. The result is a more effectively applied tissue stimulation pulse, with less shock strength required for cardioversion.

Figure 11:
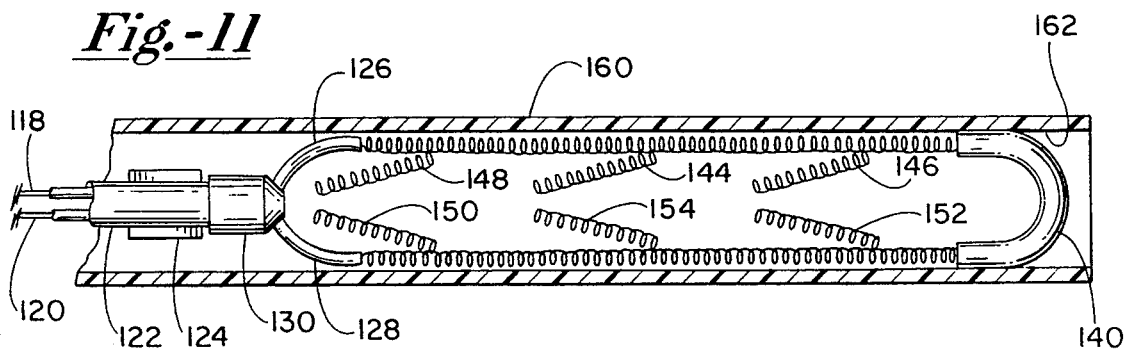
FIG. 11 is a view of the electrode array contained within a deployment device in a delivery configuration.

A delivery cannula 160 is used in the placing and releasing the electrode array. As seen in FIG. 11, the lead catheter, sleeves, and electrodes including branch segments are resiliently compressed within a lumen 162 of delivery cannula 160, in the same manner as the previously discussed electrode array. Electrodes 132 and 134 are inserted into the pericardial space through a subxiphoid or subcostal incision, again in the same manner as previously described. FIGS. 12 and 13 illustrate one preferred manner of positioning electrodes 132 and 134. Electrode 132 is positioned along the left ventricle 164, with electrode 134 positioned along the right ventricle 166. The pericardium tends to maintain the electrodes against epicardial tissue. The electrode branch segments, having been released from delivery cannula 160, resiliently assume their somewhat parallel, interdigitating configuration, with electrodes 132 and 134 cooperating to form the single, closed loop array in wrapping engagement around the heart. The branch segments preferably are centered over lateral aspects of the right and left ventricles. Electrodes 132 and 134 are maintained physically separate from one another by dielectric structure including the sleeves and tube connector. Accordingly, they can be independently and differently biased, to provide a complete cardioversion/defibrillation system. Of course, an intravenously inserted electrode can be provided as well, e.g. in the superior vena cava, if desired.

All of the preceding embodiments concern cardioversion/defibrillation, for terminating potentially life-threatening tachyarrhythmias. It is to be appreciated that tissue stimulation electrode configurations for other purposes, e.g. cardiac pacing for preventing or terminating tachyarrhythmias, can be constructed according to the present invention. In any event, the tissue stimulation device can incorporate two or more differently polarized electrodes, deployed simultaneously within a single catheter and using minimally invasive surgical procedures. The approach is well suited for deploying several electrodes within the pericardial space, although other locations within the thoracic region can be selected as desired. The closed loop electrode configuration is particularly favorable, in that suturing or otherwise anchoring the lead catheter is sufficient to anchor the electrodes, there being no need for hooks, barbs or other auxiliary fasteners along the electrodes themselves. The loop configuration also lends itself well to a selective reshaping of the electrodes after release, for example, using the disclosed inextensible filament. Finally, electrode branch segments can be projected inwardly of the loop, to substantially reduce potential gradients over effective electrode shocking surface areas.

What is claimed is:

1. A body implantable device for conducting tissue stimulation pulses generated by an electrical pulse generator, including:

an electrode array comprising a resilient, elongate and electrically conductive first electrode; an elongate resilient and electrically conductive second electrode; and an electrically insulative connecting means for securing the first and second electrodes relative to one another, said electrode array tending to assume a loop configuration when in a relaxed state, each of the first and second electrodes having an exterior surface exposed over a majority of the electrode length and being electrically isolated from the other electrode when the electrode array is in the loop configuration;

an elongate and flexible first conductor having a distal end portion electrically coupled to the first electrode and a proximal end adapted for coupling to an electrical pulse generator, for conducting electrical pulses between the pulse generator and the first electrode;

an elongate and flexible second conductor having a distal end region electrically coupled to the second electrode and a proximal end adapted for coupling to the pulse generator, for conducting electrical pulses between the pulse generator and the second electrode, said first and second conductors being electrically isolated from one another;

an electrode deployment means operatively associated with the electrode array for confining the electrode array elastically compressed against a restoring force in a delivery configuration to facilitate a body insertion and delivery of the electrode array to a predetermined stimulation site within the body, the deployment means being controllable from along a proximal region of the first and second conductors to effect a release of the electrode array at the stimulation site, whereupon the electrode array returns to the loop configuration under the restoring force; and a control means coupled to the electrode array for selectively elastically deforming the electrode array, after said release, out of the loop configuration and into an implant configuration in which the first and second electrodes remain electrically isolated from one another.

2. The device of claim 1, wherein:

said electrode array has respective proximal and distal ends, and the control means comprises a substantially inextensible filament attached at a distal end thereof to the electrode array, said filament being moveable proximally relative to the first and second conductors to elastically deform the electrode array into the implant configuration.

3. The device of claim 2 further including:

a latching means for maintaining a proximal portion of the filament and securing the filament against distal movement responsive to an elastic restoring force of the electrode array, thereby to maintain the electrode array in the implant configuration.

4. The device of claim 3 wherein:

said filament has a filament distal end and said first and second conductors have respective first and second distal ends: and the latching means comprises a spherical bead mounted to the filament distal end, and a bead retaining member at the first and second distal ends of said first and second conductors, said bead retaining member including means for capturing and maintaining the bead, to prevent distal movement of the filament, relative to the bead retaining member.

5. The device of claim 1 further including:

a lead catheter containing the first and second conductors and having a lead catheter distal end disposed proximate the distal end portion and distal end region of the first and second conductors respectively.

6. The device of claim 5 further including:

an anchoring means proximate the distal end of the lead catheter, for securing the lead catheter to body tissue.

7. The device of claim 5 wherein:

said first and second electrodes have respective first and second distal end portions; and the electrically insulative connecting means includes the distal end of the lead catheter and an insulative coupling sleeve fixed to the respective first and second distal end portions of the first and second electrodes to maintain the first and second distal end portions in spaced apart relation to one another.

8. The device of claim 7 further including:

a substantially inextensible filament attached to the insulative coupling sleeve and moveable proximally to move the insulative coupling sleeve proximally following said release, thus to elastically deform the electrode array into an implant configuration in which the first and second electrodes remain electrically isolated from one another.

9. The device of claim 8 further including:

a spherical bead mounted integrally to the inextensible filament and located at least proximate the insulative coupling sleeve, and a bead retaining member at the distal end of the lead catheter for capturing and retaining the bead upon sufficient proximal movement of the filament.

10. The device of claim 8 wherein:

the electrode array forms a single closed loop when in the loop configuration, and forms two loops when in the implant configuration.

11. The device of claim 1 wherein:

the deployment means comprises a deployment cannula having a lumen containing the first and second conductors and further containing the electrode array along a distal region of the deployment cannula, said deployment cannula being slidable proximally relative to the conductors and the electrode array to release the electrode array.

12. The device of claim 1 further including:

a plurality of electrode branch segments, each branch segment coupled at one end to one of the first and second electrodes; and wherein the electrode array when in the loop configuration forms at least one substantially closed loop, with the branch segments extended inwardly of the at least one closed loop.

13. A body implantable device for conducting tissue stimulation pulses generated by an electrical pulse generator, including:

a resilient electrode means for stimulating tissue including at least one elongate resilient curvelinear electrode having an exposed exterior surface over the majority of its length and curvelinear when in a relaxed state to define a loop, the electrode means further including a plurality of substantially linear electrode branch segments, each branch segment electrically coupled at one end to the curvelinear electrode and directed inwardly of the loop;

an elongate and flexible conductor means having a distal end region electrically coupled to the at least one curvelinear electrode and having a proximal end adapted for coupling to an electrical pulse generator for conducting electrical pulses between the pulse generator and the electrode means; and an electrode deployment means for releasably confining the electrode means in a compressed delivery configuration against an elastic restoring force, to facilitate a body insertion and delivery of the electrode means to a predetermined stimulation site within the body, the electrode deployment means being controllable to release the electrode means, whereupon the electrode means returns to the relaxed state under the restoring force.

14. The device of claim 13 wherein:

said electrode means includes first and second elongate resilient curvelinear electrodes, and an insulative connecting means for supporting the first and second electrodes with respect to one another and maintaining the first and second electrodes electrically isolated from one another when in the relaxed state;

wherein the conductor means includes elongate and flexible first and second conductors electrically isolated from one another and coupled at respective distal end regions thereof to the first and second curvelinear electrodes, respectively, the conductors further having respective proximal ends adapted for coupling to the pulse generator; and wherein the plurality of electrode branch segments includes a first set of the branch segments coupled to the first curvelinear electrode, and a second set of the branch segments coupled to the second curvelinear electrode.

15. The device of claim 14 further including:

a lead catheter containing the first and second conductors, with a distal end of the lead catheter proximate the respective distal end regions of the first and second conductors.

16. The device of claim 15 further including:

an anchoring means mounted to the lead catheter near the distal end, for securing the lead catheter to body tissue.

17. A process for implanting a plurality of electrodes epicardially in electrical isolation from one another, including the steps of:

providing a deployment device having a lumen and a distal end with an electrode array comprising a plurality of electrodes contained in the lumen in an elastically compressed delivery configuration, with a plurality of electrical conductors contained in the lumen electrically isolated from one another and proximally of the electrodes and having respective distal end regions, one of the conductors electrically coupled to each of the electrodes;

inserting the distal end of the deployment device into a body through a subxiphoid, subcostal or intercostal incision, and moving the deployment device distally until the distal end enters a pericardial space through a pericardial incision;

positioning the distal end near a predetermined epicardial stimulation site to align the electrodes with the stimulation site;

proximally withdrawing the deployment device while maintaining the electrodes so aligned, to release the electrode array from the deployment device whereupon the electrode array, under an elastic restoring force, assumes a loop configuration in which the electrodes are maintained in electrical isolation from one another at the predetermined epicardial stimulation site; and following deployment, selectively elastically deforming the electrode array into an implant configuration including a plurality of loops, with the electrodes remaining electrically isolated from one another.

18. The process of claim 17 including the further step of:

following deployment, securing the electrodes against any substantial movement by securing the distal end regions of the conductors to body tissue.

19. The process of claim 17 including the further step of:

anchoring the distal end regions of the conductors to body tissue, to prevent any substantial migration of the electrodes.

20. The process of claim 17 including the further step of:

connecting the respective conductors to different terminals of a pulse generator, and operating the pulse generator to cause transmission of electrical pulses from one of the electrodes to the other via cardiac tissue.

* * * * *

UNITED STATES PATENT AND TRADEMARK OFFICE
CERTIFICATE OF CORRECTION

PATENT NO. : 5,397,342
DATED : March 14, 1995
INVENTOR(S) : Ronald W. Heil, Jr., Bruce H. KenKnight, Robert W. Wickham, Jr.

It is certified that error appears in the above-indentified patent and that said Letters Patent is hereby corrected as shown below:

Title page, item [75], Inventor:
"Bruce H. Kenknight" should read -- Bruce H. KenKnight --.

Signed and Sealed this

Twentieth Day of June, 1995

Attest:

BRUCE LEHMAN

Attesting Officer

Commissioner of Patents and Trademarks